United States Patent [19]
Guigan

[11] Patent Number: 5,061,446
[45] Date of Patent: Oct. 29, 1991

[54] DEVICE FOR PERFORMING BIOLOGICAL ANALYSES BY IMMUNOENZYMATIC DETECTION OF ANTIBODIES OR ANTIGENS IN A SERUM

[76] Inventor: Jean Guigan, 5, rue des Ursulines, 75005 Paris, France

[21] Appl. No.: 381,429

[22] Filed: Jul. 18, 1989

[30] Foreign Application Priority Data

Jul. 28, 1988 [FR] France .................. 88 10211

[51] Int. Cl.⁵ .............. G01N 9/30; G01N 21/00; B04B 5/02
[52] U.S. Cl. ................. 422/64; 422/72; 422/100; 422/102; 436/45; 436/810; 356/246; 356/247; 494/16; 494/21
[58] Field of Search ............ 422/64, 72, 100, 102; 436/45, 810; 356/246, 427; 494/16, 21

[56] References Cited

U.S. PATENT DOCUMENTS

| 3,726,645 | 4/1973 | Kaczmarek. | |
|---|---|---|---|
| 4,119,407 | 10/1978 | Goldstein et al. | 422/72 |
| 4,470,954 | 9/1984 | Chiknas | 422/72 |
| 4,673,653 | 6/1987 | Guigan | 436/809 |
| 4,676,952 | 6/1987 | Edelmann et al. | 422/64 |
| 4,714,590 | 12/1987 | Guigan | 356/427 |
| 4,814,144 | 3/1989 | Edelmann et al. | 422/72 |
| 4,814,282 | 3/1989 | Holen et al. | 422/72 |

FOREIGN PATENT DOCUMENTS

| 166933 | 1/1986 | European Pat. Off. |
| 192968 | 9/1986 | European Pat. Off. |
| 8802866 | 4/1988 | PCT Int'l Appl. |

Primary Examiner—Robert J. Warden
Assistant Examiner—Theresa A. Trembley
Attorney, Agent, or Firm—Sughrue, Mion, Zinn Macpeak & Seas

[57] ABSTRACT

The device of the invention comprises a plurality of cartridges (1) containing serum, conjugate, substrate, blocking liquid, and a liquid-receiving well containing an antigen-carrying brush. A processing device (40) for simultaneously processing cartridges (1) considerably reduces the time required for the reaction compared with prior art devices.

9 Claims, 10 Drawing Sheets

DEVICE FOR PERFORMING BIOLOGICAL ANALYSES BY IMMUNOENZYMATIC DETECTION OF ANTIBODIES OR ANTIGENS IN A SERUM

The present invention relates to a device for performing biological analyses by immuno-enzymatic detection of antibodies or antigens in a serum.

BACKGROUND OF THE INVENTION

In outline, a known indirect solid phase immuno-enzymatic method comprises the following stages:

The serum in which antibodies are to be detected and quantified is inserted into a small size cylindrical well (about 1 cm high and 5 mm in diameter) made of plastic material; the inside surface of the well is initially coated with antigens. Time is allowed for the antibodies to fix onto the antigens.

A first washing operation is performed to eliminate the serum and an enzyme-labelled conjugate liquid is inserted, with the enzyme fixing in turn on the antigen-antibody bonds.

Washing is performed a second time to remove excess conjugate liquid.

From this stage there are two different methods of proceeding:

The first consists in using colorimetry: a colorless substrate is inserted and it develops a colored reaction in response to the residue enzyme, and the result is read in a photometer.

The second method uses luminescence: a "Signal" reagent is inserted and reading is performed by means of a luminiscence analyser.

These measurements serve to determine the quantity of antibodies or antigens present in the patient's serum.

When the method is applied conventionally, it may take five to six hours for the antibodies to fix onto the antigens, with this length of time being required to ensure that a the number of antibodies fixing onto the antigens is sufficient. The initial antigen-antibody bonds cover the surface of the well, thereby making access thereto more difficult for subsequent antibodies.

The object of the present invention is to implement a device enabling the total time required for analysis to be considerably reduced, and also limiting the number of manipulations that are essential when performing the prior method.

SUMMARY OF THE INVENTION

The present invention provides a device for performing biological analyses by immuno-enzymatic detection of antibodies or antigens in a serum, the device comprising a processing device for simultaneously processing a plurality of cartridges, the assembled device and cartridges being disposed in a thermostatically controlled enclosure, said processing device comprising:

a hub associated with a motor having an angle encoder for controlling rotation cycles of the hub and capable both of imparting rapid motion thereto for centrifuging, and of imparting or slow step-by-step motion thereto;

a plurality of cartridge-carrying lifts disposed radially on the hub and means for passing each of them from a high, "cartridge-loading" position to a low, "working" position, each of these lifts having an open peripheral face, and a top face and a bottom face which are largely open, and each lift including declutchable means for radially locking the corresponding cartridge for centrifuging;

a plurality of reading gauges fixed to said hub, level with respective peripheral faces of said lifts;

each cartridge is generally rectangular in shape comprising a bottom of thermoformed plastic material covered with a thin transparent sheet of plastic material and thus constituting:

a collecting cuvette disposed in a central position and connected by a duct to a serum storage cuvette situated at the end of the cartridge which is intended to be located adjacent to said hub;

at least two cuvettes between the collecting cuvette and said serum storage cuvette, said at least two cuvettes being connected via respective ducts to said collecting cuvette, and being intended respectively to contain a sachet of conjugate liquid and a sachet of substrate liquid, said collecting cuvette having a small liquid-evacuation hole in its bottom and containing a substantially cylindrical well closed by a lid, and rotatable about a vertical axis, with a portion of the side wall of the well forming a pouring or receiving spout for all of the liquids that may flow in the above-mentioned ducts, and which contains a brush having a large surface area per unit volume and which is rotatable about a vertical axis independently of said well, with the bristles of said brush carrying antigens; and a flexible pocket for containing a diluting or blocking liquid and connected by a duct to said collecting cuvette, and situated close to the open peripheral face of the corresponding lift, said duct being closed by a breakable capsule;

the processing device further comprising at least one peripheral read module situated on the trajectory of said gauges and a module situated above the trajectory of said cartridges and provided with means for rupturing said sachets respectively containing the conjugate and the substrate, and also with means for breaking said breakable capsule.

Preferably, said processing device is associated with at least one pipette for automatically filling the corresponding cuvettes of said cartridges with serum.

Said processing device advantageously also includes a module for automatically loading a cartridge into each lift, as well as a module for automatically unloading cartridges.

In an improvement, said processing device includes a module provided with means for pressing against said flexible pocket and ensuring that the liquids contained therein are homogenized.

In an advantageous embodiment, the vertical axis of said brush is fixed to a small metal star suitable for co-operating with a module of said processing device, which module is provided with an electromagnet situated level with the trajectory of said vertical axis in such a manner as to cause the brush to rotate regularly about its axis. This same module may also include an electromagnet suitable for co-operating with the lid or the bottom of said well having external metalization in order to rotate said well about its axis towards a first position where the pouring spout points to said evacuation hole and towards a second position where the pouring spout points towards the duct leading to said flexible pocket.

In addition, said module situated over the trajectory of said cartridges includes hammers controllable by electromagnets and suitable for flattening said sachets, with a cutting member being provided between the bottoms of the sachets and the cuvettes in which they are received, said module also including a hammer suitable for breaking said breakable capsule.

Advantageously, each reading gauge is constituted by a transparent member substantially in the form of a gutter serving to lock said flexible pocket radially in position, said means for locking the cartridges in their lifts then being disengaged, said gutter having two horizontal side walls at a calibrated distance apart against which said flexible pocket bears while centrifuging is taking place.

BRIEF DESCRIPTION OF THE DRAWINGS

An embodiment of the invention is described by way of example with reference to the accompanying drawings, in which.

DETAILED DESCRIPTION

Figure 1:
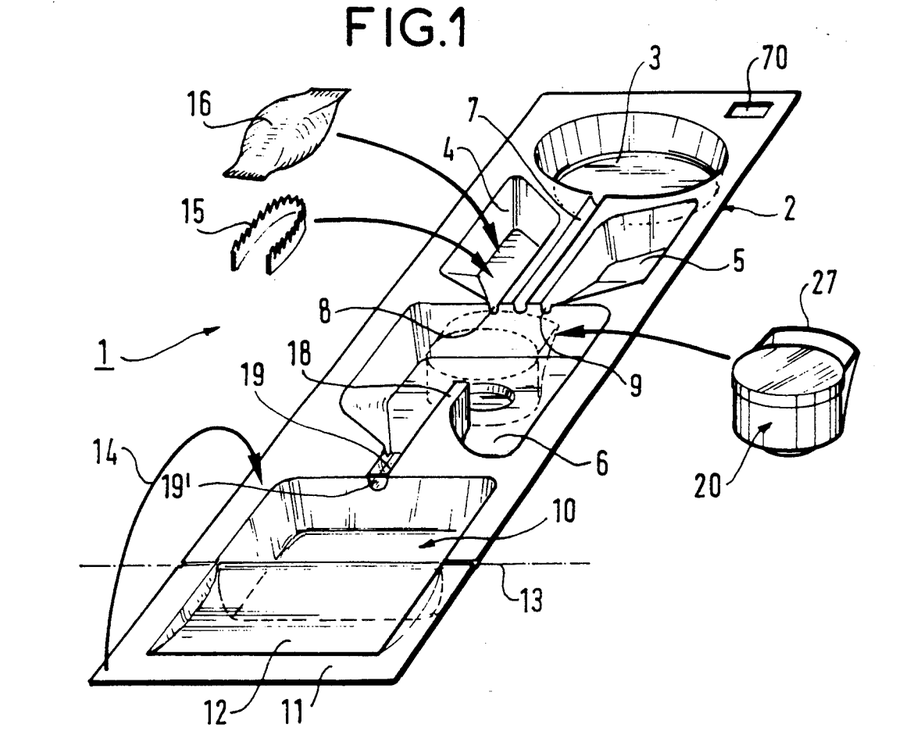
FIG. 1 is a partially exploded fragmentary perspective view of an analysis cartridge of the invention.
Figure 2:
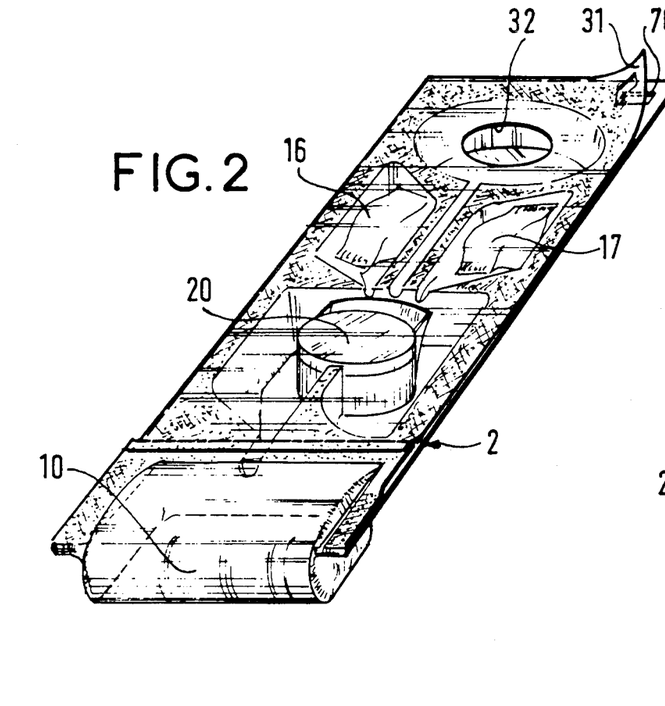
FIG. 2 is a perspective view of the FIG. 1 cartridge.
Figure 3:
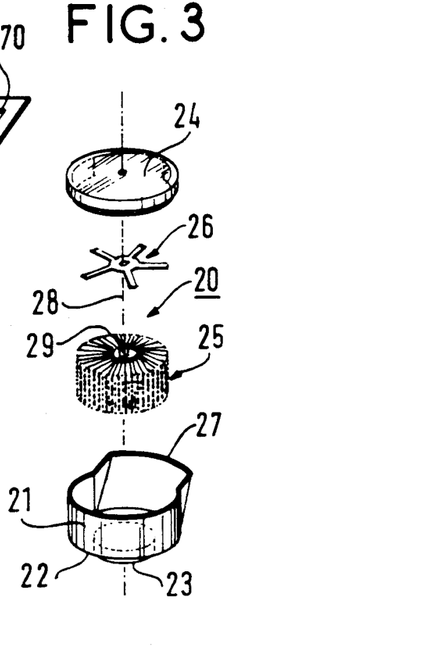
FIG. 3 is an exploded view of the well belonging to the cartridge shown in FIGS. 1 and 2.
Figure 4:
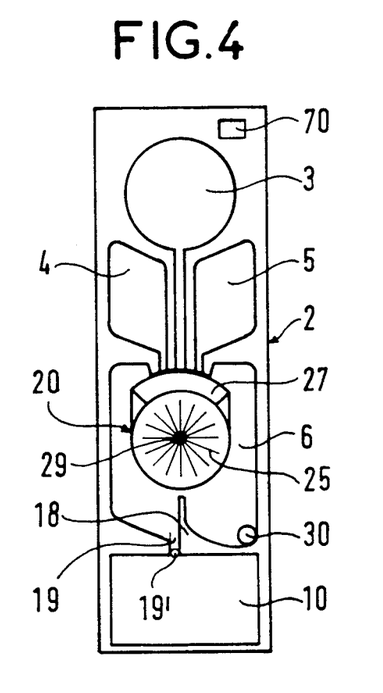
FIGS. 4 to 6 are highly diagrammatic plan views of the above cartridge showing the FIG. 3 well in three different positions.

FIGS. 1, 2, and 3 are perspective views of a cartridge 1 suitable for replacing the small tube used in the prior art. Such a cartridge is constituted as follows (see FIG. 1). It comprises a bottom 2 made of thermoformable plastic material, e.g. polystyrene, which is generally rectangular in shape and which includes a plurality of storage cuvettes:

a cuvette 3 for storing serum and situated at a first end;

a cuvette 4 for storing an enzyme-labelled conjugate;

a cuvette 5 for storing a substrate capable of being hydrolized by said enzyme;

a collecting cuvette 6 communicating with each of said cuvettes 3, 4, and 5 via respective ducts 7, 8, and 9. In addition to the well 20 described in greater detail below, the collecting cuvette 6 has a side opposite to the three ducts 7, 8, and 9 including two zones separated by a wall 18, with the first zone communicating with the following pocket 10 via a duct 19 and with the second zone communicating with the outside via a hole 30 provided through the bottom 2 and visible in FIGS. 4 to 6; and an analysis pocket 10 formed by folding over onto the bottom 2 a portion 11 which is thermoformed to have a hollow 12 and which is folded about an axis 13 in the direction of arrow 14. The analysis pocket 10 is more clearly visible in FIG. 2 and is closed by hot welding. Initially, communication between the pocket 10 and the duct 19 is closed by a breakable capsule 19'. Prior to being completely closed, the pocket 10 is partially filled with a diluting or blocking liquid.

Cuvettes 4 and 5 initially contain respective cutting members on their bottoms and shown diagrammatically at 15, together with respective sachets containing the conjugate or the substrate. FIG. 2 shows the sachet 16 containing the conjugate and the sachet 17 containing the substrate.

Figure 5:
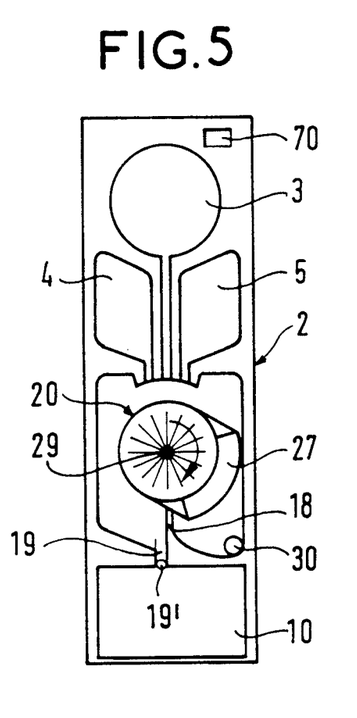
Figure 6:
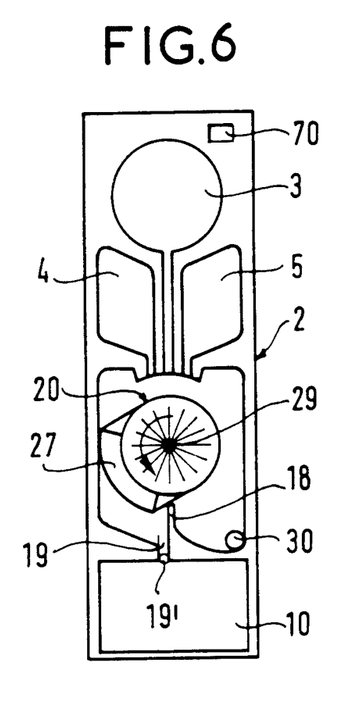

The collecting cuvette 6 contains a fundamental element of the invention, namely the well 20 made of plastic material. It comprises (see FIG. 3) a hollow body 21 provided with a bottom 22 having a projection 23 for engaging in the bottom 2 of the cartridge 1; a portion of the side wall of the hollow body 21 is formed to have a pouring spout 27 which is normally pointed towards the serum-storing cuvette 3, as shown in FIGS. 1 and 2. The shape of the spout 27 is suitable for coming just up to the ducts 7, 8, and 9 in order to pick up any liquid coming from these ducts. The bottom 22 or the lid 24 of the body 21 has an external metal coating in order to cooperate with an electromagnet for the purpose of rotating the well about its axis 21 to one or other of the positions shown in FIGS. 5 and 6, respectively. In FIG. 5 the pouring spout 27 points towards the hole 30; in FIG. 6, the pouring spout 27 points towards the duct 19. In both cases, the pouring spout 27 and the wall 18 co-operate so as to delimit two distinct pouring zones.

The essential portion of the well 20 (cf. FIG. 3) is a small bottle brush 25 having an axis 29 and fixed to a small metal star 26. As described below, the small star 26 responds to the action of an electromagnet by rotating the brush 25 regularly about its axis 29.

When everything is in position in the various cuvettes in the bottom 2, the cartridge is closed by being covered with a thin film of Surlyn 31 (trademark belonging to Du Pont de Nemours), having an opening 32 over the serum storage cuvette 3 and which is hot welded to the non-thermoformed walls of the bottom 2 (see FIG. 2).

By way of example, the cartridge may be 50 mm long, 15 mm wide, and a little more than 10 mm high. The well 20 has an inside diameter of 7 mm and a height of 10 mm. The film of Suryln is about 40 microns thick. The cuvettes 3, 4, and 5 are intended respectively to receive:

100 microliters to 200 microliters of serum;
100 microliters of conjugate; and
100 microliters of substrate.

The pocket 10 may receive 250 microliters of blocking or other liquid.

The above-defined cartridge is provided with identification means and is intended to be processed in a device 40 as shown in FIGS. 7 to 12 and constituting a mini-laboratory. The device is generally in the form of a rectangular box 50 having a square base with a side of 300 mm, and about 200 mm high. It is placed in a thermostatically controlled enclosure, preferably at a temperature of 37° C.

Figure 7:
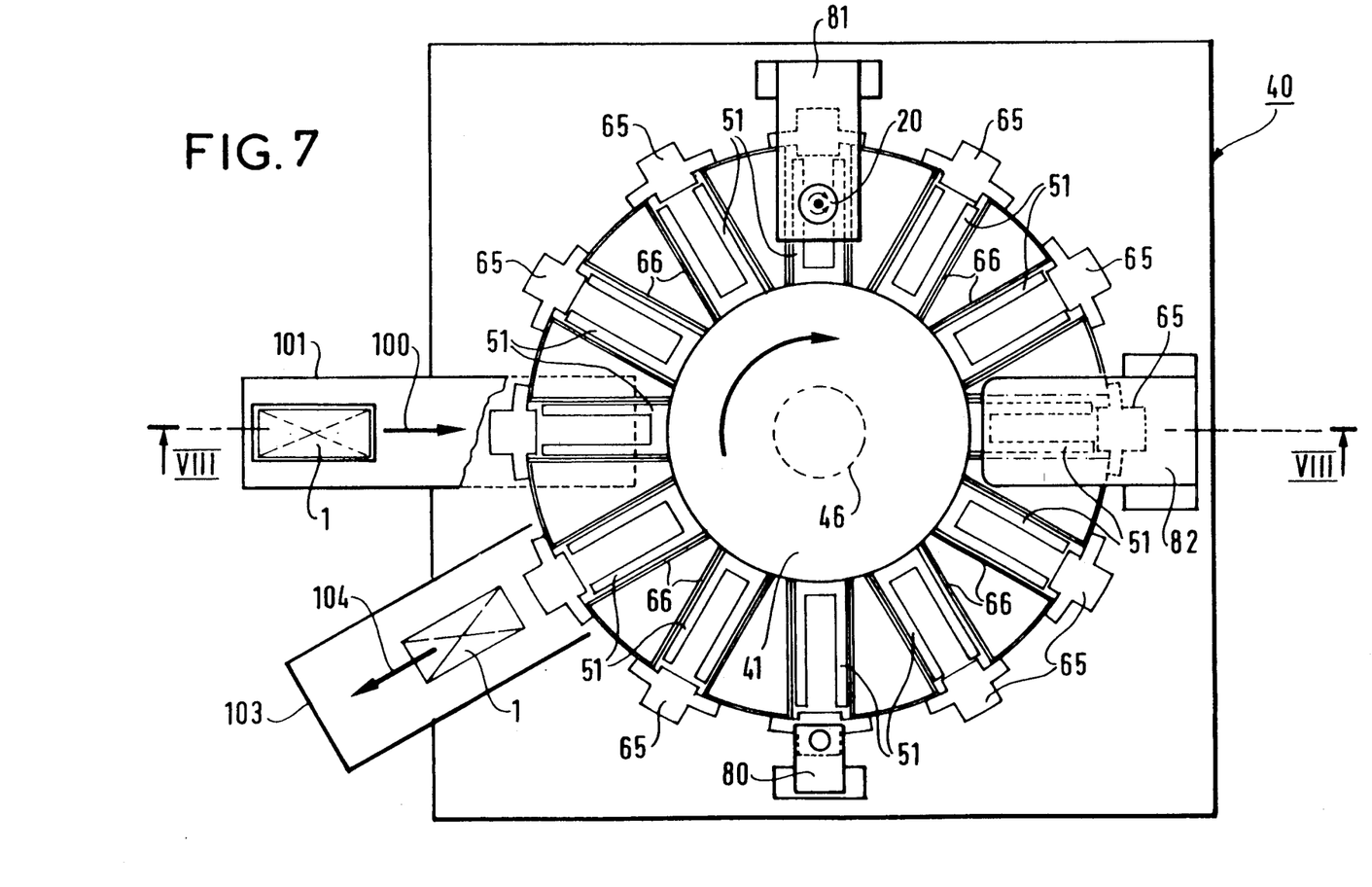
FIG. 7 is a diagrammatic plan view of a cartridge processing device.
Figure 8:
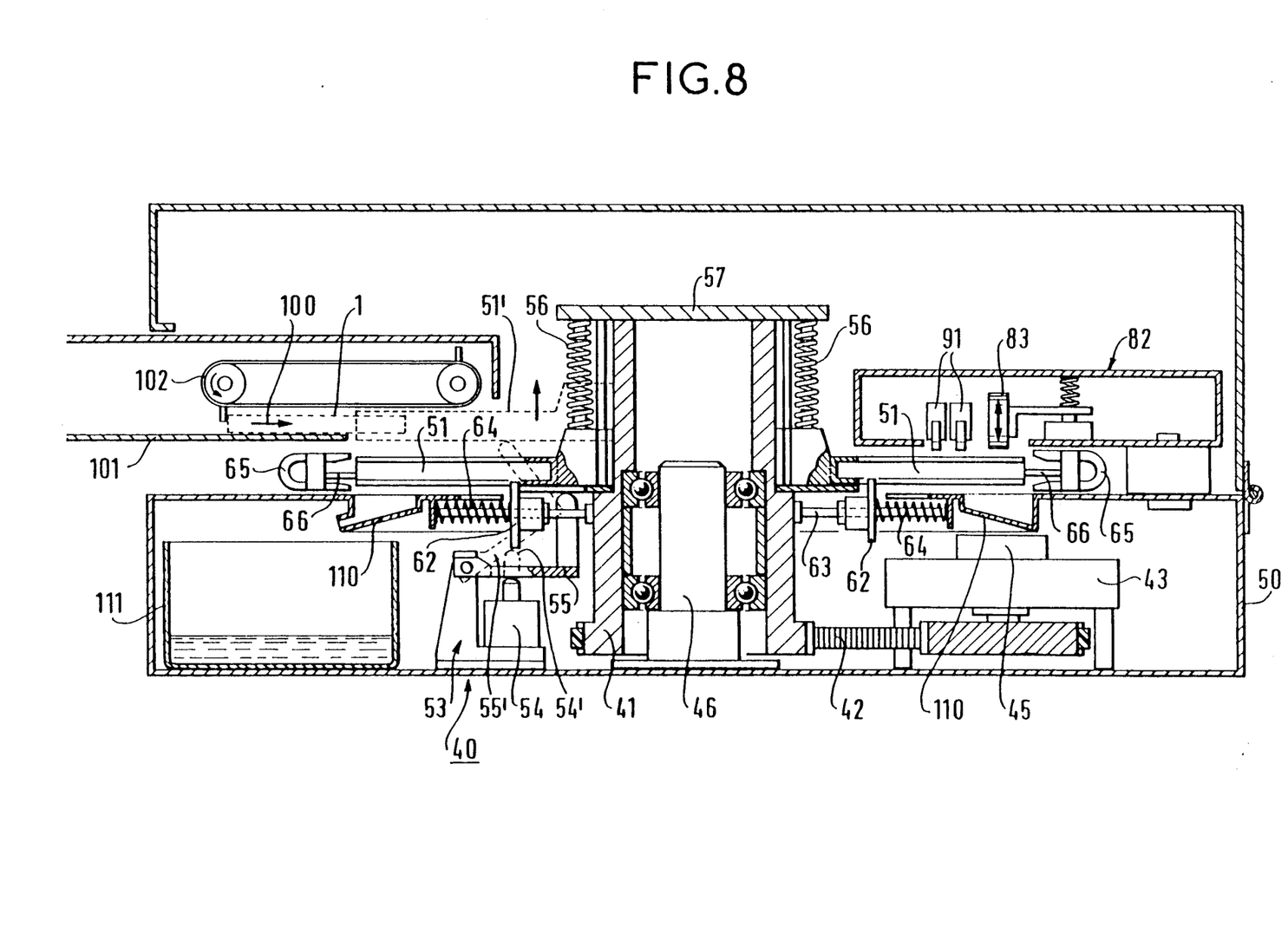
FIG. 8 is a diagrammatic section view on line VIII—VIII of FIG. 7.

The main subassemblies of the device 40 are the following (cf. FIGS. 7 and 8).

A hub 41 capable of being rotated on a shaft 46 by a motor 43 via a transmission system represented diagrammatically at 42 and including a cog belt and two toothed wheels. The motor is a D.C. motor associated with an angle encoder 45 for measuring rotation cycles.

The hub 41 is fixed to twelve cartridge-carrying lifts such as 51 which are distributed uniformly radialy thereabout. Each cartridge-carrying lift 51 is associated with a control system 53 for moving the cartridge-carrying lift 51 from a raised position 51' shown in dashed lines to a lowered position shown in solid lines. The control system 53 may be constituted by a controllable electromagnet 54 associated with a lever 55. Positions 54' and 55' of the electromagnet and the lever and shown in dashed lines correspond to the position 51' of the cartridge-carrying lift 51. Return springs 56 are provided between the lifts 51 and the top face 57 of the hub 41.

When the lift is in position 51', a cartridge 1 can be inserted therein manually along arrow 100 as shown in FIG. 8. This insertion is preferably performed by an automatic loading module 101 (with drive shown diagrammatically at 102). Similarly there is an automatic unloading module 103 operating in the direction indicated by arrow 104 and shown in FIG. 7.

Figure 9:
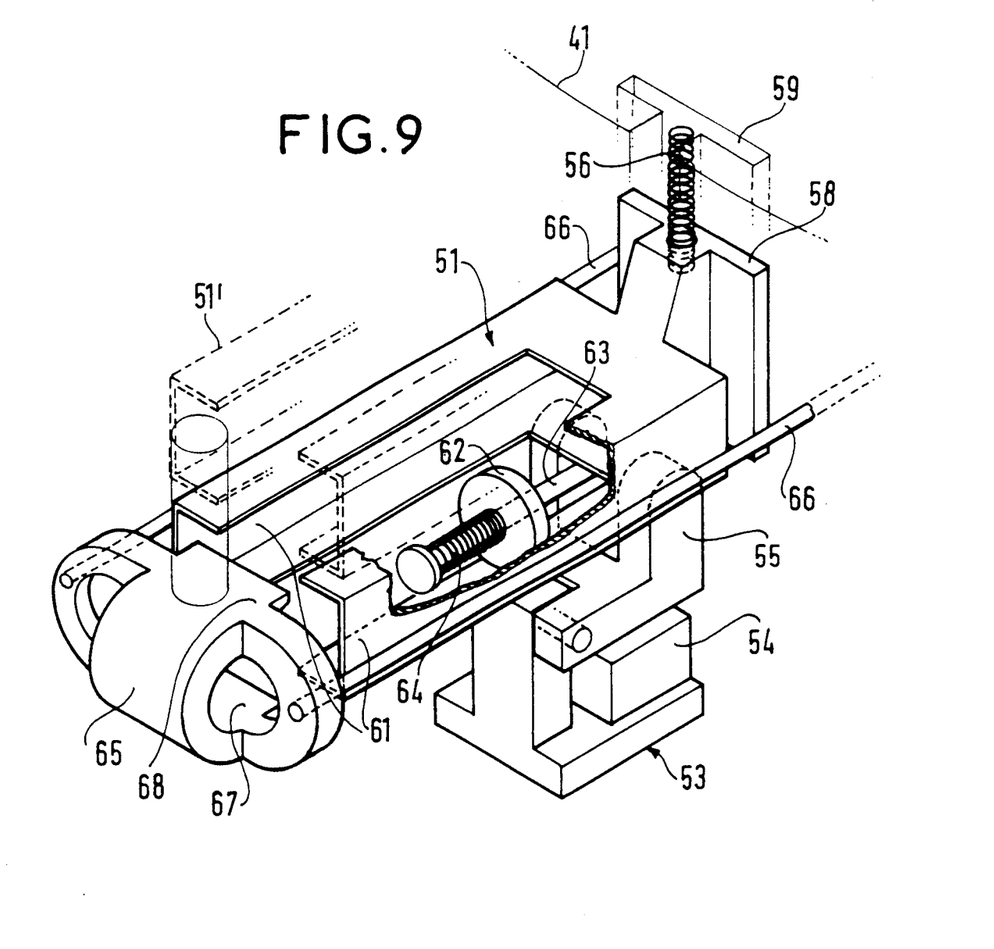
FIG. 9 is a diagrammatic perspective view of a cartridge-carrying lift belonging to the device of FIGS. 7 and 8.

FIG. 9 shows a lift 51 in greater detail, the lift comprising a T-shaped portion 58 guided in a corresponding groove 59 of the hub 41. On the opposite side, the lift 51 has its inlet face open, and on its side portions it is formed with channel section rails 61, and its top face is also wide open. The same applies to its bottom, through which there projects a cartridge indexing disk 62 suitable for sliding on a rod 63 fixed to the hub 41 and co-operating with a return spring 64 which is more clearly visible in FIG. 10. This figure also shows a notch 74 provided in the cartridge 1 and in which the disk 62 is received. This system is suitable for driving the cartridge 1 towards the outlet face of the lift 51 in the direction of arrow 69. In contrast, the system shown in FIG. 11 and co-operating with an orifice 70 of the cartridge 1 is intended to hold it nearer the center of the hub when it is in the position shown by solid lines. This system is constituted by a moving arm 72 associated with a return spring 75 and actuated by a controllable electromagnet 71. The arm 72 can take up a position 72' with its end 73 inserted in the orifice 70 then taking up position 73', and thus leaving the orifice. The cartridge 1 is then driven by the system shown in FIG. 10 which guides it radially towards the periphery of the device 40.

At the periphery of the device 40 and level with each inlet face of a lift 51, there is an optical reader gauge 65 fixed to the hub 41, e.g. by rods 66. Each gauge 65 is constituted by a part which is substantially gutter shaped (see FIGS. 7 and 9) which is open at its ends, and which has an accurately determined gap between side walls 67 and 68. It may be a part made from injected polycarbonate which is completely transparent.

FIG. 7 shows the module 80 for reading reactions by colorimetry, or by luminescence, or by any other appropriate method, by looking through the gauges 65. This figure also shows a module 81 housing the electromagnets for performing the rotary maneuvers on the wells 20 in the cartridges 1, and a module 82 which is shown in greater detail in FIG. 12. The module 82 firstly includes a rolling wheel 83 which rotates in the direction of arrow 84 and which is fixed to the end of an arm 85 that rocks about an axis 86 enabling the rolling wheel 83 to be retracted. The arm is controlled by an electromagnet 87 and a return spring 88 fixed to the module 82. The rolling wheel 83 lies over the location of pocket 10. The module 82 also includes hammers 91 and 92 which rock about respective axes 93 and 94 under the control of electromagnets 95 and 96. These hammers lie over the sachets 16 and 17 containing reagents and overlying cutting members 15. Another hammer 97 is situated over the location of the breakable capsule 19' for the purpose of breaking it when required.

Finally, the device 40 includes a fixed annular drain tank 110 beneath the lifts 51 (see FIG. 8) connected to a removable tank 111.

The various stages of using a cartridge 1 in the processing device 40 are described below.

When the cartridge 1 is inserted via the automatic loading module 101 into a cartridge-carrying lift while in position 51' (see FIG. 8), it is in the state shown in FIG. 2, i.e. both sachets 16 and 17 are in place, there is a blocking liquid 120 in the flexible pocket 10, and the brush 25 is in the well 20 and has antigens fixed to its bristles. Since the effective surface area of the brush 25 is very much greater than that of a prior art well, the well 20 contains a quantity of antigens spread over a very much larger area.

Figure 10:
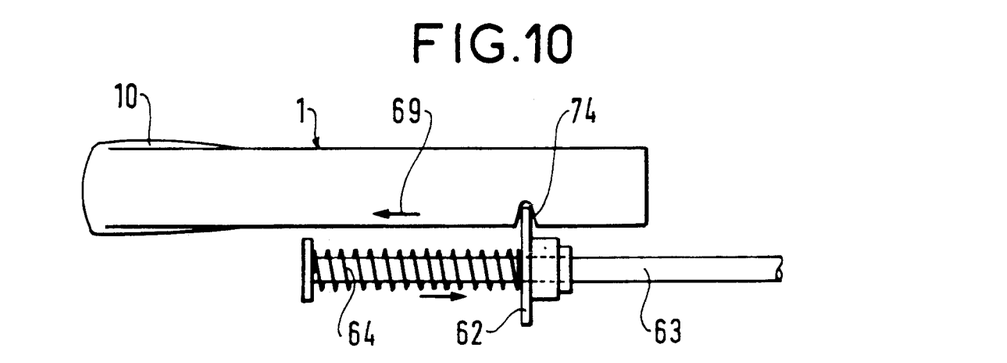
FIG. 10 is a diagrammatic side view of a first cartridge return system belonging to the cartridge-carrying lift of FIG. 9.
Figure 11:
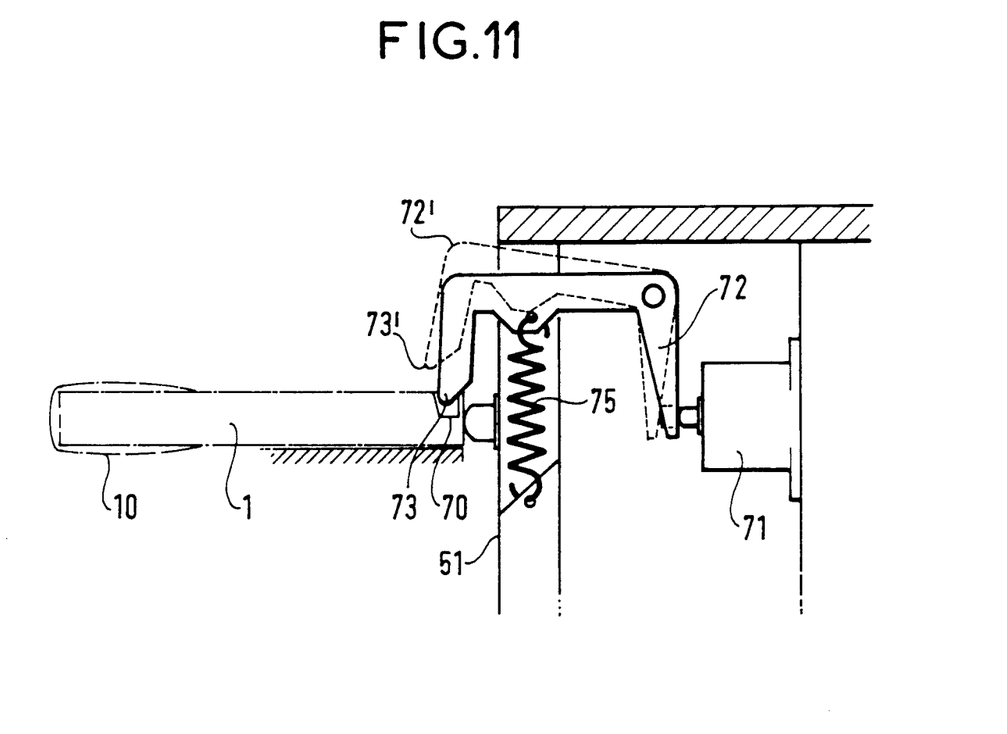
FIG. 11 is a diagrammatic side view of a second cartridge return system belonging to the cartridge-carrying lift of FIG. 9.
Figure 12:
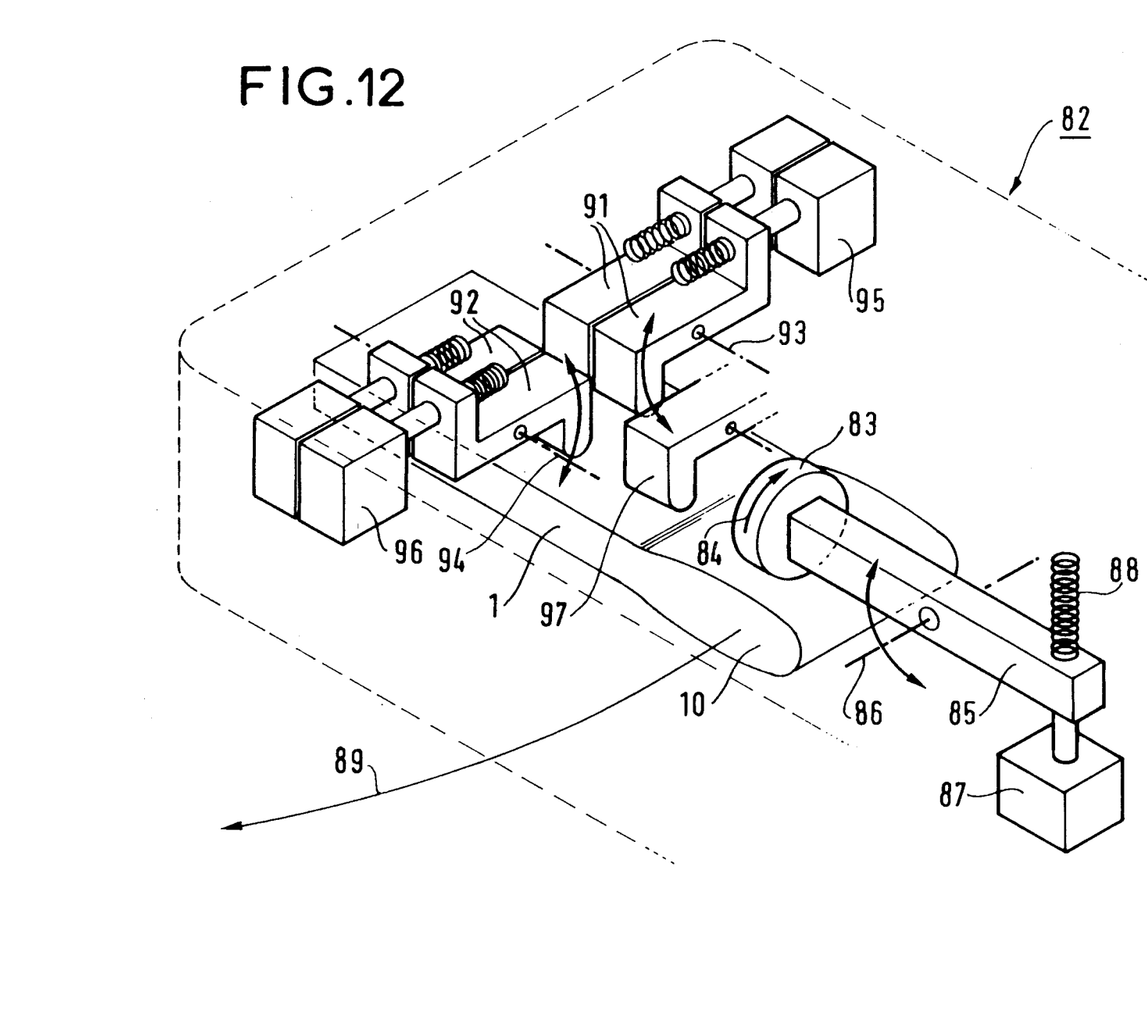
FIG. 12 is a diagrammatic perspective view of a module belonging to the above processing device.
Figure 13:
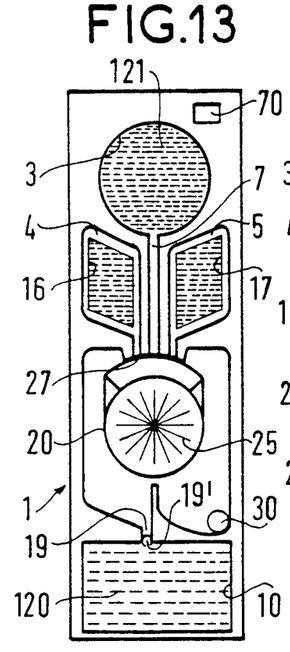
FIGS. 13 to 30 are diagrams showing the different reaction stages which take place in a cartridge.

When loaded, the cartridge 1 engages the system illustrated in FIGS. 10 and 11 by means of its orifice 70 and its notch 74 (see FIG. 10). Once the cartridge-carrying lift has returned to position 51, the motor 43 rotates the hub 41 through one-twelfth of a turn so as to enable the next cartridge to be loaded (FIGS. 7 and 8). While the second cartridge is being loaded, it is advantageous to insert serum 121 into cuvette 3 of the first cartridge. This may be done automatically, for example by using the pipette described in the present Applicant's French patent application number 87 15688. The cartridge is then in the state illustrated in FIG. 13.

Figure 14:
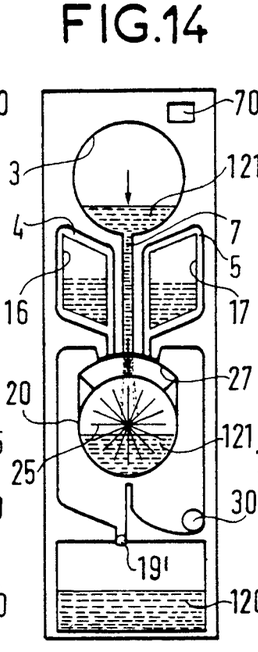
Figure 15:
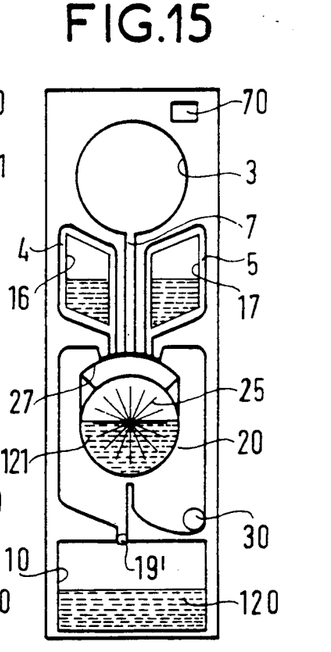

Once all of the cartridges have been loaded, the hub 41 is rotated for centrifuging so as to cause the serum 121 to flow along the duct 7 into the well 20 (FIGS. 14 and 15). The serum then comes into contact with the antigens and any anti-bodies there may be in the serum fix onto the antigens. This operation takes several tens of minutes. During this time, the hub 41 rotates uniformly so that the cartridges stop successively beneath the module 81 (FIG. 7) whose electromagnet rotates the small metal star 26 through one-fifth of a turn, thereby also rotating the brush 25 which is always about half immersed. By virtue of this rotation, each bristle of the brush 25 goes through the immersed position enabling it to collect antibodies and then to the non-immersed position in which it is completely cleared of antibody-poor serum. This serum stirring motion and the very large surface area of the brush make it possible to obtain antigen-antibody fixing in a considerably shorter period of time than is possible in prior methods (cf. FIG. 15).

Figure 16:
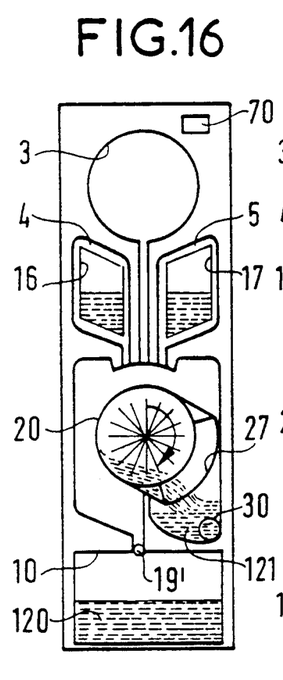

After a few tens of minutes, the cartridge 1 passes the module 81 in which one of the electromagnets is operated so as to rotate the well 20 as shown in FIG. 16 so that its pouring spout 27 points towards the hole 30 via which the antibody-poor serum 121 is evacuated. The serum ends up in the annular tank 110 (FIG. 8). After being emptied, and while still in place beneath the module 81, the cartridge 1 has its well 20 returned to its initial position. Then by using a pipette (not shown) several tens of microliters of washing water 122 are inserted into cuvette 3. The cartridge is then centrifuged (cf. FIG. 17) and the water 122 enters the well 20.

The hub 21 continues to rotate, and each time it goes through the module 81, the brush rotates about its own axis so that all of its bristles are washed. After a few minutes, the cartridge is held stationary beneath the module 81, as shown in FIG. 16, in order to rotate the well 20 to point towards the hole 30 so as to evacuate the washing water 122 (cf. FIG. 18).

Figure 19:
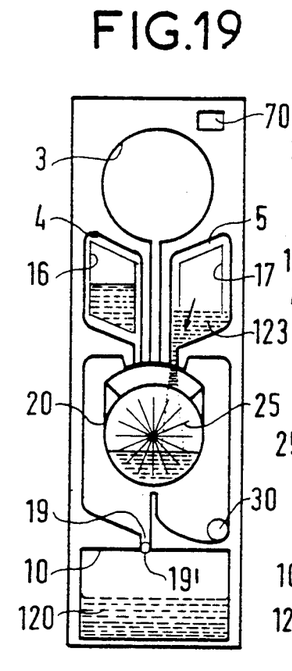
Figure 20:
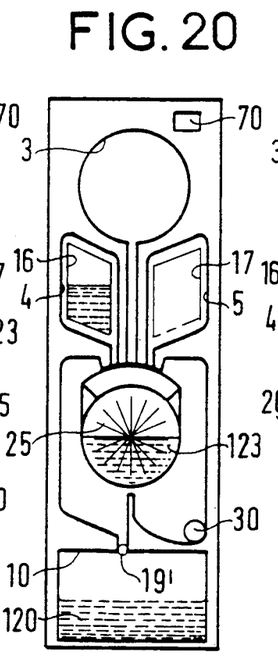

The cartridge 1 then passes beneath the module 82 (cf. FIG. 12) and the electromagnet 95 acts on the hammers 91 which compress the sachet 17 against the cutting member 5. The sachet 17 is burst and the enzyme-labelled conjugate liquid 123 can escape. Centrifuging brings it into the well 20 where it comes into contact with the bristles on the brush (cf. FIGS. 19 and 20). Hereagain, the brush is rotated about its own axis for several minutes so that the conjugate 123 can fix on all of the antigen-antibody bonds.

Figure 21:
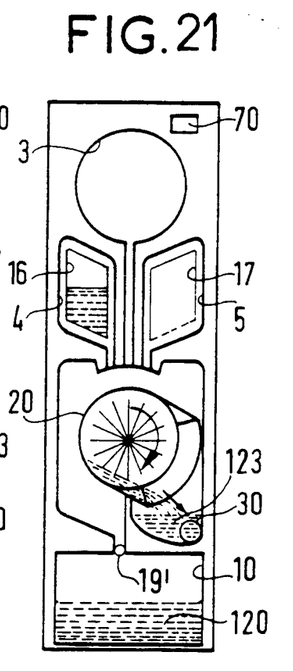

Thereafter, the conjugate 123 is eliminated by rotating the well 20 to point to the hole 30 (cf. FIG. 21).

Figure 17:
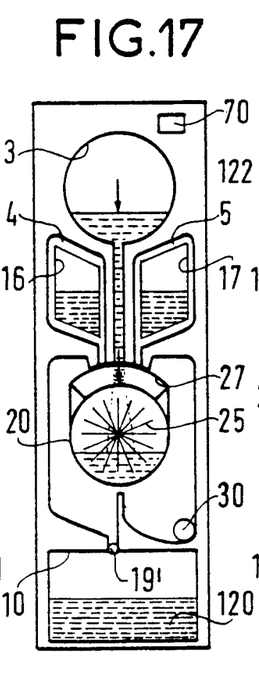
Figure 18:
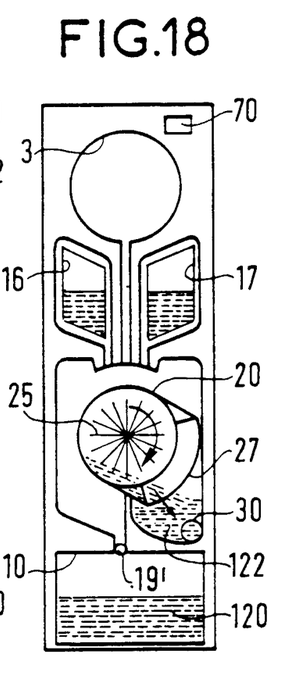
Figure 22:
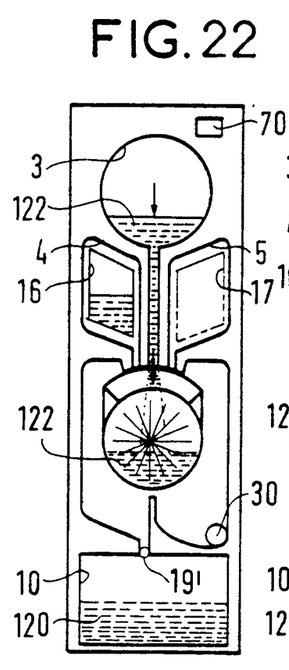
Figure 23:
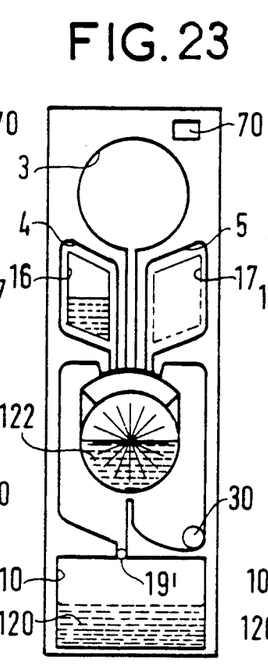
Figure 24:
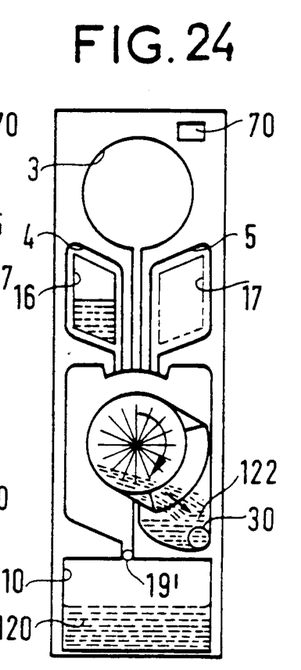

The washing operation of FIGS. 17 and 18 is repeated in successive stages which appear in FIGS. 22 to 24.

Figure 25:
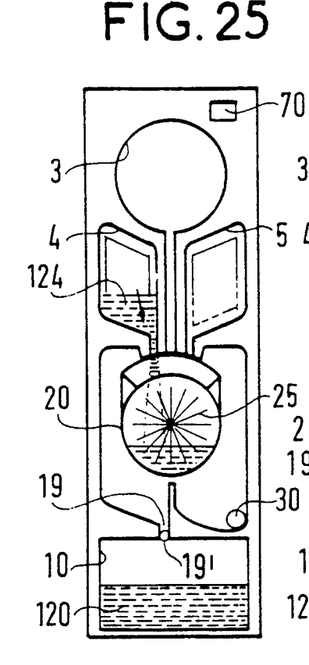
Figures 26, 27:
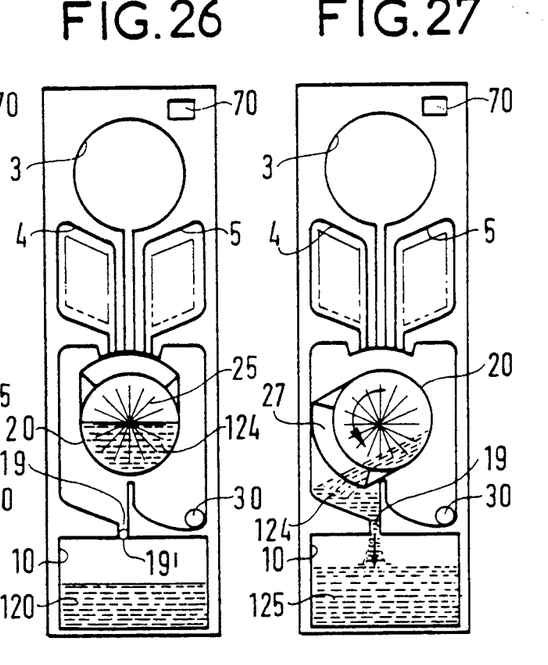

When the cartridge 1 goes back under the module 82 (cf. FIG. 12), the hammers 92 act on the sachet 16 which bursts like the sachet 17, thereby releasing substrate 124. Centrifuging puts this substrate into contact with the brush 25 (cf. FIGS. 25 and 26). A colored reaction develops for several minutes during which the brush 25 is rotated about it axis. On passing through the module 82 (cf. FIG. 12), the hammer 97 breaks the breakable capsule 19' and opens communication between the cuvette 6 and the flexible pocket 10. The well 20 is rotated so that its pouring spout 27 points towards the duct 19, and after a further centrifuging operation, the liquid 124 passes into the pocket 10, where the reaction is fixed (cf. FIG. 27).

These various successive centrifuging operations have the advantage of eliminating any wetting effect on the bristles of the brush and of successively eliminating all liquid excesses inserted into the well.

Figure 28:
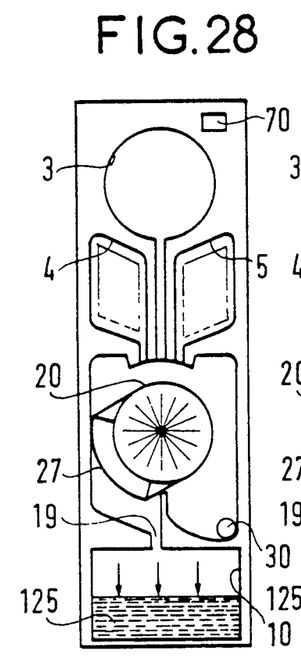
Figures 29, 30:
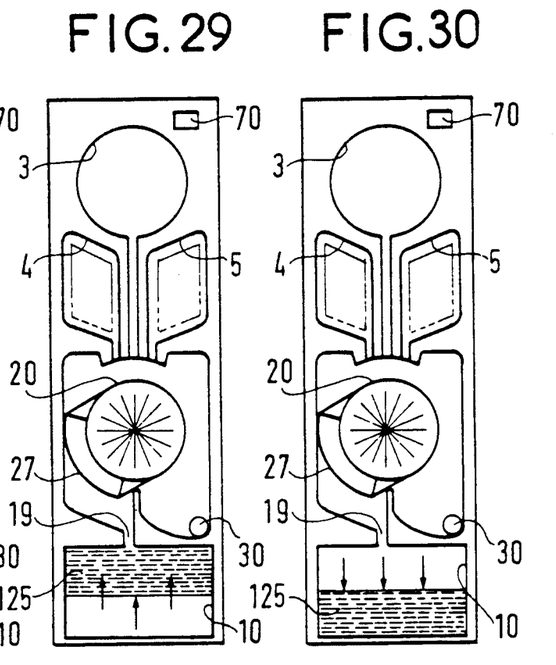

When the cartridge 1 goes through the module 82 (cf. FIG. 12), the roller wheel 83 is pressed against the pocket 10 by the electromagnet 87 and the arm 85 and rotates on its own axis, thereby homogenizing the mixture 125 (cf. FIGS. 28 to 30). The cartridge 1 is then ready to be examined.

The electromagnet of FIG. 11 then acts on the arm 72 which takes up position 72', thereby releasing the cartridge 1 which is then urged towards the periphery of the device by the spring 64 shown in FIG. 10. Under the effect of centrifuging, the flexible pocket 10 partially filled with liquid 25 presses against the plane walls 67 and 68 disposed at a calibrated distance apart in the gauge 25 associated therewith (cf. FIG. 9). Measurement is then performed by colorimetry, or by luminescence, or by any other appropriate method when the cartridge 1 goes through the measurement module 80.

The operation of the device 40 is controlled by a programmed computer. The device 40 associated with cartridges 1 is thus capable of automatically performing reliably and accurately all of the operations required for immuno-enzymatic detection, and it can do this in a much shorter period of time than is required by prior art devices. The fixing of the antibodies on the antigens now requires only a few tens of minutes, while the other stages require only a few minutes each.

Naturally, the invention is not limited to the embodiment described above. Any means may be replaced by equivalent means without going beyond the scope of the invention. Thus, for example, the brush could be replaced by an element having an equivalent developed surface area.

In order to clarify the drawing, only twelve cartride-carrying lifts are shown, but the dimensions mentioned above actually leave room for eighteen of them, but again this number is merely an example.

I claim:

1. In combination, a device for performing biological analyses by immuno-enzymatic detection of antibodies or antigens in a serum and a plurality of cartridges, the device comprising a processing device for simultaneously processing said plurality of cartridges, said cartridges being assembled to said device and said cartridges being disposed in a thermostatically controlled enclosure, said processing device comprising:

a hub associated with a motor having an angle encoder for controlling rotation cycles of the hub and capable both of imparting rapid motion thereto for centrifuging, and of imparting or slow step-by-step motion thereto;

a plurality of cartridge-carrying lifts disposed radially on the hub, means for passing each of said lifts from a high, "cartridge-loading" position to a low, "working" position, each of said lifts having an open peripheral face, a top face and a bottom face which are largely open, and each lift including declutchable means for radially locking the corresponding cartridge for centrifuging;

a plurality of optical reading gauges fixed to said hub, level with respective peripheral faces of said lifts for optically viewing the contents of said cartridges;

each of said cartridges being generally rectangular in shape comprising a bottom of thermoformed plastic material covered with a thin transparent sheet of plastic material and constituting:

a collecting cuvette disposed in a central position and connected by a duct to a serum storage cuvette situated at the end of the cartridge located adjacent to said hub;

at least two cuvettes between the collecting cuvette and said serum storage cuvette, said at least two cuvettes being connected via respective ducts to said collecting cuvette, for containing respectively, a sachet of conjugate liquid and a sachet of substrate liquid; said collecting cuvette having a small liquid-evacuation hole in a bottom and containing a substantially cylindrical well closed by a lid, said well being rotatable about a vertical axis, and having a portion of a side wall of the well forming a spout for all of the liquids flowing in the said ducts, and containing a brush having a large surface area per unit volume, said brush being rotatable about a vertical axis independently of said well, with the bristles of said brush carrying antigens; and a flexible pocket for containing a diluting or blocking liquid connected by a duct to said collecting cuvette, and situated close to an open peripheral face of the corresponding lift, said duct being closed by a breakable capsule; and the processing device further comprising at least one peripheral read module situated on the path of said gauges and a module situated above the path of said cartridges provided with means for rupturing said sachets respectively containing the conjugate and the substrate, and also means for breaking said breakable capsule.

2. A device according to claim 1, wherein said processing device is operatively associated with at least one pipette for automatically filling the corresponding cuvettes of said cartridges with serum.

3. A device according to claim 1, further including a module for automatically loading a cartridge into each lift.

4. A device according to claim 1, further including a module for automatically unloading cartridges.

5. A device according to claim 1, further including a module provided with means for pressing against said flexible pocket for homogenizing liquids contained therein.

6. A device according to claim 1, wherein a vertical axis of said brush is fixed to a small metal star cooperating with a module of said processing device and provided with an electromagnet situated level with the path of said vertical axis to cause the brush to rotate regularly about said axis.

7. A device according to claim 6, wherein the module for moving said brush also includes an electromagnet cooperating with one of the lid or the bottom of said well and having external metalization to rotate said well about its axis towards a first position where the spout points to said evacuation hole and towards a second position where the spout points towards the duct leading to said flexible pocket.

8. A device according to claim 1, wherein said module situated over the of said cartridges includes hammers controllable by electromagnets for flattening said sachets, and a cutting member being provided between the bottoms of the sachets and cuvettes in which said sachets are received, and said module further also including a hammer for breaking said breakable capsule.

9. A device according to claim 1, wherein each said reading gauge is constituted by a transparent member substantially in the form of a gutter locking said flexible pocket radially in position, wherein said means for locking the cartridges in their lifts is then disengaged, and said gutter having two horizontal side walls at a calibrated distance apart against which said flexible pocket bears while centrifuging is taking place.

* * * * *